United States Patent [19]

Mustranta et al.

[11] Patent Number: 5,932,452
[45] Date of Patent: Aug. 3, 1999

[54] PROCESS FOR THE PRODUCTION OF XYLOSE BY HYDROLYSIS OF HEMICELLULOSE BY IMMOBILIZED ENZYMES

[75] Inventors: Annikka Mustranta, Espoo; Kaisa Poutanen, Helsinki; Heikki Heikkilä, Espoo; Marja-Leena Sarkki, Kantvik, all of Finland

[73] Assignee: Xyrofin Oy, Helsinki, Finland

[21] Appl. No.: 08/289,803

[22] PCT Filed: Sep. 21, 1990

[86] PCT No.: PCT/FI90/00206

§ 371 Date: Mar. 27, 1992

§ 102(e) Date: Mar. 27, 1992

[87] PCT Pub. No.: WO91/03566

PCT Pub. Date: Mar. 21, 1991

Related U.S. Application Data

[63] Continuation of application No. 07/838,287, Mar. 27, 1992, abandoned.

[30] Foreign Application Priority Data

Sep. 6, 1989 [FI] Finland ..................................... 894206

[51] Int. Cl.⁶ .................................................. C12P 19/02
[52] U.S. Cl. .......................................... 435/105; 435/200
[58] Field of Search ..................................... 435/101, 174, 435/105, 200

[56] References Cited

U.S. PATENT DOCUMENTS

| | | | |
|---|---|---|---|
| 4,168,250 | 9/1979 | Sutthoff | 260/174 |
| 4,200,692 | 4/1980 | Puls | 435/99 |
| 4,226,938 | 10/1980 | Yoshida | 435/176 |
| 4,275,159 | 6/1981 | Puls | 435/179 |
| 5,130,243 | 7/1992 | Kimura | 435/95 |
| 5,328,841 | 7/1994 | Lorch | 435/209 |

FOREIGN PATENT DOCUMENTS

| | | |
|---|---|---|
| 0189864 | 1/1986 | European Pat. Off. . |
| 0297912 | 6/1988 | European Pat. Off. . |
| 1597436 | 4/1978 | United Kingdom . |
| 2131812 | 12/1982 | United Kingdom . |

OTHER PUBLICATIONS

Oskar, Zaborsky, Ph.D.; *Immobilized Enzymes*, pp. 5–27, Published by Esso Research and Engineering Company, Linden, New Jersey; published by CRC Press, a Division of The Chemical Rubber Co., Cleveland, Ohio.

Paul Allenza, Dale S. Scherl and Robert W. Detroy, and Timothy D. Leathers; Hydrolysis of Xylan by an Immobilized Xylanase from *Aureobasidium pullulans*; Biotechnology and Bioengineering Symp. No. 17 (1986), pp. 425–433; Published 1987 John Wiley and Sons, Inc.

C.Y. Jenq, S.S. Wang and B. Davidson; Ultrafiltration of raw sewage using an immobilized enzyme membrane; Department of Chemical and Biochemical Engineering, Rutgers University, New Brunswick, New Jersey, USA; Received Jul. 10, 1979; revised Nov. 7, 1979).

"Heran Laktoosin Hydrolyysi immobilisoidalla β—galaktosidaasilla" (Hydrolysis of whey lactose by means of immobilized β—galactosidase), Master's thesis by K. Hyrkäs at Helsinki University of Technology, 1974, pp.39–47.

Chemical Abstracts vol. 96 (1982), 64847w.
Chemical Abstracts vol. 98 (1983), 177464d.
Chemical Abstracts vol. 96 (1982), 124760z.
Chemical Abstracts vol. 100 (1984), 99098f.
Chemical Abstracts vol. 100 (1984) 33246w.
Weckstrom et al, Adv. Biotechnol., vol. 2, 1981, pp. 21–26.
Linko et al., Enzyme Eng. (1980), 5, 305–8.

*Primary Examiner*—Irene Marx
*Attorney, Agent, or Firm*—Kenyon & Kenyon

[57] ABSTRACT

The invention relates to a process for the hydrolysis of a hemicellulose substrate containing xylo-oligomers with an immobilized enzyme by adjusting the pH of an aqueous solution containing hemicellulose oligosaccharides and optionally ionic components to a value within a weakly acidic range, and contacting the solution with a hemicellulolytic enzyme or mixture of enzymes immobilized on a regenerable weak cation exchange carrier without fixing additives, and recovering xylose from the solution. The invention also concerns an enzyme preparation to be used in the process, comprising a weak cation exchange carrier and a hemicellulolytic enzyme or mixture of enzymes immobilized on said carrier.

13 Claims, No Drawings

PROCESS FOR THE PRODUCTION OF XYLOSE BY HYDROLYSIS OF HEMICELLULOSE BY IMMOBILIZED ENZYMES

This application is a continuation of application Ser. No. 07/838,287, filed on Mar. 27, 1992 now abandoned.

The invention relates to a process for the hydrolysis of a hemicellulose substrate containing xylo-oligomers by hemicellulolytic enzymes immobilized by adsorbing on a solid carrier. The invention further concerns a combination of a solid carrier and a hemicellulolytic enzyme or mixture of enzymes immobilized on the carrier for realizing this process of hydrolysis. The process is well suited for the production of xylose from xylo-oligomers containing spent liquors of cellulose industries and from the water extracts of steam-exploded plant material.

Hemicellulolytic enzymes, i.e. hemicellulases, include xylanase, β-xylosidase and esterases, which actively cleave hemicellulosic material through hydrolysis. Among these xylanase and esterase enzymes cleave the xylan and acetyl side chains of birch xylan and the remaining xylo-oligomers are unsubstituted and can thus be hydrolysed with β-xylosidase only. In addition, several less known side activities have been found in enzyme preparations which hydrolyse hemicellulose. Hemicellulolytic enzymes are produced by the fermentation of certain microorganisms, such as fungi of the Aspergillus or Trichoderma genera. The culture medium as such or enzyme fractions separated from it can be used as an enzyme preparation in the hydrolysis of hemicellulose.

Under hydrolytic reaction conditions hemicellulolytic enzymes free in a solution retain their activity only for a relatively short period of time. They are expensive to use and difficult to recover. Enzymes immobilized on a solid carrier are more stable than free enzymes, and they are also more easily reusable, wherefore several processes have been developed for immobilizing hemicellulolytic enzymes.

One major problem in the hydrolysis of a technical hemicellulose solution by immobilized enzyme is the high salt content of the solution. An ionic material shows a tendency to displace the enzyme from the surface of the carrier so that the column loses rapidly its enzyme activity.

Hemicellulolytic enzymes have been immobilized, for example, on silica gel, alumina, or steel (Oguntimeim, G. B., Proc. Annu. Biochem, Eng. Symp. 1978, vol. 8, p. 27–37), on porous glass (Rogalski, J. et al., Enzyme Microb. Technol. 7 (1985) No. 8, p. 27–37), on fibres (Tavobilov, I. et al.; Chemical Abstracts 104 (1986) 30924n) or on benzoquinone silochrome carrier (Balcere D. et al.; Chemical Abstracts 100 (1984) 99098f). The use of silica gel carrier has also been suggested by Shimizu (Biotechnology and Bioengineering, 29 (1987) p. 36–241) and Allenza et al. (Biotechnology and Bioengineering Symp. No. 17 (1986) John Wiley & Sons 1987). Puls J. et al. (Trans. Tech. Sect., Can. Pulp Pap. Assoc. 3 p. 64–72 and U.S. Pat. No. 4,275,159) have used porous glass beads, silica gel beads and sea sand as carrier in the immobilization of hemicellulase and xylanase fractions.

In all these prior art immobilization techniques, the enzyme is fixed onto the carrier using an additive which activates the surface of the carrier and/or forms a covalent bond between the carrier and the enzyme. In the process described in the above-mentioned U.S. Pat. No. 4,275,159 (Puls et al.) an enzyme fraction containing mainly xylanase and an enzyme fraction containing mainly β-xylosidase are immobilized separately on different carriers using in both cases glutaraldehyde, carbodiimide or $TiCl_4$ as a fixing additive, and the resulting two enzyme preparations are used in the hydrolysis of xylan.

Oguntimein et al. (Biotechnol. Bioeng. 22 (1980) p. 1127–1142) have studied the immobilization of β-xylosidase purified from a commercial enzyme preparation produced by *Aspergillus niger* on ten different carriers. It was found that the immobilization was very difficult to perform and satisfactory results with regard to activity and stability were obtained only with an enzyme fixed with $TiCl_4$ on alumina and with an enzyme fixed with glutaraldehyde on porous alkyl amine silica gel.

Weckström, L. and Leisola, M. (Advances in Biotechnology. Edit. M. Moo-Young and C. W. Robinson, Proc. 6th Inter. Ferment. Symp. London Canada Jul. 20–25 1980, Pergamon Press 1981, p. 21–26) have studied the hydrolysis of xylan contained in sulphite spent liquor by an enzyme preparation produced by *Aspergillus niger* and fixed onto phenol formaldehyde resin (DUOLITE S 761) with glutaraldehyde. In a control experiment, the enzyme was adsorbed on the carrier without fixing additive. The experiments showed that the use of glutaraldehyde is necessary to maintain the adsorbed enzyme activity in the resin. With glutaraldehyde the half-life of the immobilized enzyme preparation was about 30 days.

It is also well-known that ampholytic proteins such as enzymes can be adsorbed on ion exchangers. This adsorption has been utilized to isolate pure enzymes from various solutions. U.S. Pat. No. 4,168,250 discloses one way of immobilizing enzyme on an ion exchange carrier. From European Patent 222838 (Davies et al. 1987) it is known to immobilize gammaglobulin on a strong anion exchanger.

A drawback of the prior art processes of immobilizing hemicellulolytic enzymes is that the enzyme activity level does not always remain satisfactory for a sufficiently long period of time; on the other hand, due to the fixing additive used in the immobilization, the regeneration of the carrier is too complicated to be applied in industrial processes.

The object of the invention is to provide a process of hydrolysing a hemicellulose solution by immobilized enzyme in such a manner that the enzyme retains its activity substantially undeteriorated for long periods of time. The carrier is easy to regenerate and the hemicellulose substrate can be a hemicellulose solution containing high levels of ionic components, such as spent liquor from cellulose industries and an aqueous extract of a steam exploded plant material.

These objects are achieved according to the invention by using a hemicellulolytic enzyme or a mixture of enzymes which is immobilized on a weak cation exchange carrier without fixing additive.

Thus the invention concerns a process of hydrolysing a hemicellulose solution containing xylo-oligomers, which process is characterized by adjusting the pH of a solution of hemicellulose to a value within a weakly acidic range, and contacting the solution with a hemicellulolytic enzyme immobilized on a weak cation exchange carrier without the addition of fixing additives. The invention concerns further an enzyme preparation useful in this process and comprising a weak cation exchange carrier and a hemicellulolytic enzyme or mixture of enzymes immobilized on the carrier without fixing additives.

The invention is based on the unexpected finding that a hemicellulolytic enzyme, preferably β-xylosidase, can be successfully immobilized on a weak cation exchange carrier. Use of enzyme fixing additives, such as glutaraldehyde, is not necessary.

Weak cation exchange carriers suited for use in the invention include macroporous acrylate resin DUOLITE C 464 and agglomerated carboxymethyl cellulose strengthened with polystyrene.

Hemicellulolytic enzymes to be used in the invention belong to a hemicellulase group usually produced by fermenting a microorganism of the Trichoderma genus. The most important xylanolytic enzymes of this group are xylanase, β-xylosidase, acetyl esterase and α-glucuronidase. These enzymes can be isolated from enzyme solutions by such known fractionating techniques as ammonium sulphate precipitation or ultrafiltration. The culture medium used in the fermentation of the microorganism as such or enzyme fractions separated from the solution can be used in the process of the invention. Preferably, the process of the invention uses a mixture of enzymes produced by the fungus *Trichoderma longibrachiatum* (former name *T. reesei*), or its fractions, such as β-xylosidase, if the xylan contained in the hemi-cellulose substrate has first been prehydrolysed into xylo-oligomers.

Immobilization is carried out simply by mixing the carrier with a buffered enzyme solution. The enzyme solution is buffered approximately within the pH range from 3.5 to 5. The enzyme solution is contacted with the carrier for 1 to 4 hours to ensure adequate fixation. If the hydrolysis is to be carried out in a column, the immobilization can be carried out in the column to be used.

The obtained enzyme preparation is very stable even at high ion concentrations. This is highly unexpected since the prior art technique is to elute enzymes from the carrier by salt solutions; from the enzyme preparation of the invention, however, they could not be separated in this way.

After the immobilized enzyme used in the hydrolysis has lost is activity, the column in use is regenerated. The exhausted enzyme is washed off, preferably with a diluted sodium hydroxide solution. Adsorbed impurities as well as the exhausted enzyme are removed in the wash. Then the carrier is restored into its original charging state by weak acid, and finally washed with water. Thereafter the column is filled with fresh enzyme solution.

If required, the carrier can be washed with more efficient techniques. Polymeric carriers are chemically stable and can be washed at high temperatures with strong chemicals. In most cases a single wash with sodium hydroxide is sufficient to restore the carrier.

When using the immobilized enzyme preparation of the invention, the carrier can be regenerated several times. For example, no notable changes were observed in the properties of the column after 6 regenerations. For process economy, the regeneration is a major advantage as the carrier materials are expensive. In the process of the invention the regeneration is easy to carry out as no fixing additives are used.

The hydrolysing process of the invention is well suited for the production of xylose from steam-exploded plant material and spent liquor from cellulose industries. If individual purified enzyme fractions are used in place of mixtures of enzymes, individual immobilized enzymes can be used in successive columns, or the substrate can be prehydrolysed partially with a free mixture of enzymes to decrease the molecular weight of oligosaccharides. Excellent results have been obtained, e.g., when using immobilized β-xylosidase in the hydrolysis of steam-exploded birch wood extract prehydrolysed enzymatically with xylanase and esterase.

In the following the invention will be illustrated in greater detail by means of examples.

The given enzyme activities are assayed as follows (Poutanen, K. and Puls, J., Characteristics of *Trichoderma reesei* β-xylosidase and its use in the hydrolysis of solubilized xylans, Applied Microbiology and Biotechnology 1988; reprinted in Publications 47, Technical Research Centre of Finland, Espoo 1988, Appendix 4):

β-xylosidase activity was assayed using 5 mM p-nitrophenyl-β-D-xylopyranoside (PNPX, Sigma N-2132) in 0.05 M citrate phosphate buffer, pH 4.5, as substrate. 200 μl of enzyme sample was incubated with 1.8 ml of substrate at 50° C. for 10 min. The reaction was stopped by adding 1 ml of 1 M sodium bicarbonate and the liberated p-nitrophenyl was measured at 400 nm. Activity was expressed in katals.

Xylanase activity was assayed using 1% beechwood xylan (prepared according to the process of Ebringerova et al., Holzforschung 21 (1967) p. 74–77) as substrate. The pulverized xylan was suspended by homogenizing and warming in 0.05 M citrate-phosphate buffer, pH 5.3. The enzyme sample (0.2 ml) was incubated with 1.8 ml of the substrate solution at 50° C. for 5 min. The reducing sugars formed were assayed by adding 3 ml of DNS-reagent (Sumner, J. B. and Somers, G. F., Dinitrosalisylic method for glucose. In: Laboratory experiments in biological chemistry, Academic Press, New York 1949, p. 38–39), boiling for 5 min, cooling and measuring the absorbance at 540 nm. The reference sugar was xylose and the activity was expressed in katals.

Acetyl esterase was assayed using 1 mM α-naphtylacetate in 0.05 M citrate buffer, pH 5.3, as substrate. The substrate was first dissolved in a small volume of ethanol. 0.2 ml of the enzyme sample was incubated with 1.8 ml of the substrate solution at 50° C. for 10 min, after which 1 ml of 0.01% Fast Corinth V Salt in 1 M acetate buffer, pH 4.3, containing 20% Tween 20 was added. The absorbance at 535 nm was read after 10 min. The activity was expressed in katals.

Suitable enzymes to be immobilized in the hydrolysing process of the invention include the enzyme preparation Multifect K, manufacturer Cultor Ltd., xylanase activity 84000 nkat/ml.

The following carrier materials were used in the examples:

Spezyme GDC, manufacturer Cultor Ltd.; an agglomerated diethylaminoethyl cellulose anion exchanger, abbreviated DEAE in the examples;

an agglomerated carboxymethyl cellulose strengthened by polystyrene, weak cation exchanger, abbreviated CMC in the examples;

DUOLITE S 761, manufacturer Duolite International, Rohm & Haas; adsorption resin, abbreviated DOULads in the examples;

DUOLITE ES 562, manufacturer Duolite International, Rohm & Haas; anion exchanger, abbreviated DUOLani in the examples;

DUOLITE C 464, manufacturer Duolite International, Rohm & Haas; weak cation exchanger, abbreviated DUOLcat in the examples;

Diatomaceous Earth Standard Super Cell, manufacturer Johns-Manville;

granular activated coal, manufacturer Chemviron CPG.

Production of CMC carrier

Agglomerated carboxymethyl cellulose carrier strengthened with polystyrene can be produced as described in U.S. Pat. Nos. 3,823,133 and 4,168,250. The polymer, the purified fibrous cellulose, the filler (such as a metal oxide or silicate) and the lubricant (such as magnesium stearate, aluminium stearate, or suitable oil) are mixed, and the mixture is heated to a plastic state in an extruder machine.

The mixture is then extruded and the cooled product is ground and screened to a mean particle size range of 100 to 1000 μm, preferably 350 to 850 μm. A carboxymethyl derivative is derived from the resulting agglomerated product strengthened with polystyrene by chloro acetic acid, using sodium sulphate to reduce the water activity in the reaction mixture. The ion exchange capacity of the prepared product is 0.1 to 0.2 mequiv/g.

Carboxymethylation is illustrated by the following example:

150 g of sodium suphate was dissolved in 335 ml of water at 40° C. 85 g 50% NaOH solution was added. 150 g of agglomerated cellulose resin strengthened with polystyrene and having a particle size of 350 to 850 μm was suspended into the resulting alkaline solution, and the suspension was heated to 70° C. 75 g of a 50% chloro acetic acid solution in water was added slowly during 1 hour followed by 65 g of 50% NaOH and finally another 75 g of 50% chloro acetic acid also during 1 hour. The suspension was then kept at 70° C. for another 30 minutes and then cooled to 40° C. The slurry was neutralized with 150 ml of 1 M sulphuric acid to pH 6.5 and decanted with water until the supernatant was clear and free from fine particles. The product was washed in water at 85° C. overnight to dissolve soluble residues, decanted again and drained. The ion exchange capacity of the obtained product was 0.16 mequiv/g.

EXAMPLE 1

An enzyme solution from *Trichoderma longibrachiatum* culture (former name *T. reesei*) was immobilized on different carriers of which two (CMC and DUOLcat) were weak cation exchangers to be used according to the invention. The activity of the enzyme solution used was as follows:

| xylanase | 13865 nkat/ml |
|---|---|
| β-xylosidase | 4200 nkat/ml |
| esterase | 720 nkat/ml |

The immobilization was carried out using the following two compositions:

| 1. | 20 g | carrier material |
|---|---|---|
|  | 96 ml | 0.05 M sodium citrate buffer (pH 5.0) |
|  | 4 ml | enzyme solution |
| 2. | 20 g | carrier material |
|  | 92 ml | 0.05 M sodium citrate buffer (pH 5.0) |
|  | 8 ml | enzyme solution. |

The carrier material was mixed with the enzyme solution at +4° C. for 4 hours. Then the mixture was filtrated and the activity of bound enzyme was measured.

For comparison, the enzymes were fixed in some experiments on glutaraldehyde (80 ml of 2.5% solution) by stirring for one hour. Residual aldehyde was washed off with about 2 l of 0.05 M sodium citrate buffer. Enzyme activities were measured again after fixation with glutaraldehyde.

Results from these immobilization tests are shown in the following TABLES 1 to 3. In all the experiments, the enzyme activities were measured before ("bound" in the tables) and after ("fixed" in the tables) fixation with glutaraldehyde.

TABLE 1

Xylanase activity

| Activity nkat/g | Carrier | | | | | | |
|---|---|---|---|---|---|---|---|
|  | DEAE | CMC | Diatom. earth | Act. coal | DUOLads | DUOLani | DUOLcat |
| 1. | | | | | | | |
| Offered | 1128 | 1128 | 1128 | 1128 | 1128 | 1128 | 1128 |
| Bound | 113 | 491 | 397 | 609 | 1113 | 600 | 742 |
| Fixed | 98 | 452 | 108 | 44 | 171 | 48 | 241 |
| 2. | | | | | | | |
| Offered | 2256 | 2256 | 2256 | 2256 | 2256 | 2256 | 2256 |
| Bound | 226 | 1241 | 835 | 1717 | 2195 | 957 | 1439 |
| Fixed | 179 | 1075 | 182 | 64 | 246 | 138 | 570 |

TABLE 2

β-xylosidase activity

| Activity nkat/g | Carrier | | | | | | |
|---|---|---|---|---|---|---|---|
|  | DEAE | CMC | Diatom. earth | Act. coal | DUOLads | DUOLani | DUOLcat |
| 1. | | | | | | | |
| Offered | 393 | 393 | 393 | 393 | 393 | 393 | 393 |
| Bound | 42 | 294 | 392 | 265 | 261 | 140 | 383 |
| Fixed | 41 | 220 | 181 | 1 | 129 | 56 | 69 |
| 2. | | | | | | | |
| Offered | 786 | 786 | 786 | 786 | 786 | 786 | 786 |

TABLE 2-continued

β-xylosidase activity

| Activity nkat/g | Carrier | | | | | | |
|---|---|---|---|---|---|---|---|
| | DEAE | CMC | Diatom. earth | Act. coal | DUOLads | DUOLani | DUOLcat |
| Bound | 700 | 610 | 776 | 606 | 478 | 277 | 753 |
| Fixed | 70 | 439 | 370 | 0.5 | 276 | 158 | 226 |

TABLE 3

Esterase activity

| Activity nkat/g | Carrier | | | | | | |
|---|---|---|---|---|---|---|---|
| | DEAE | CMC | Diatom. earth | Act. coal | DUOLads | DUOLani | DUOLcat |
| 1. | | | | | | | |
| Offered | 72.5 | 72.5 | 72.5 | 72.5 | 72.5 | 72.5 | 72.5 |
| Bound | 32.5 | 57.6 | 63.1 | 59.0 | 70.9 | 64.4 | 41.9 |
| Fixed | 30.0 | 72.3 | 62.0 | 0.2 | 55.3 | 34.1 | 32.0 |
| 2. | | | | | | | |
| Offered | 145 | 145 | 145 | 145 | 145 | 145 | 145 |
| Bound | 65.4 | 97.7 | 114.0 | 134.0 | 136.9 | 133.0 | 87.4 |
| Fixed | 54.0 | 136.0 | 109.0 | 0.2 | 135.0 | 96.5 | 56.4 |

As appears from TABLES 1 to 3, all enzymes are adsorbed on the weak cation exchangers (CMC and DUOLcat), and the immobilized products show high total activities. The fixing with glutaraldehyde did not improve the system.

EXAMPLE 2

The hydrolysing effect of the immobilized enzymes was tested in column experiments. The column experiments were carried out in 4 laboratory scale columns. The column size was 50 ml or 100 ml. The enzyme was immobilized on the columns by immersing the carriers in the enzyme solution for 4 hours. The carriers were then washed with a citrate buffer solution. The 50 ml columns were filled with the immobilized enzyme/carrier preparation without further treatment. The 100 ml columns were filled with an enzyme/carrier preparation which for comparison was treated with glutaraldehyde (GA) (1 hour) to fix the enzymes.

Analysis of the enzyme solution used in the immobilization:

| | |
|---|---|
| β-xylosidase | 552 nkat/ml |
| xylanase | 25000 nkat/ml |
| esterase | 240 nkat/ml |

Immobilization:

| | |
|---|---|
| 50 ml | enzyme solution |
| 350 ml | 0.05 M citrate buffer pH 5 |
| 100 g | carrier |

The characteristics of the resulting immobilized systems appear from the following TABLE 4.

TABLE 4

Immobilization of enzymes on CMC and DUOLITE C 464 carriers

| | Enzyme activity, nkat/g carrier | | |
|---|---|---|---|
| | β-xylosidase | xylanse | esterase |
| CMC carrier | | | |
| Enzyme added | 520 | 14700 | 200 |
| Enzyme adsorbed | 374 | 9540 | 150 |
| Activity in carrier | 346 | 2970 | 126 |
| Activity after GA fixation | 300 | 3180 | 137 |
| DUOLITE carrier | | | |
| Enzyme added | 364 | 10288 | 140 |
| Enzyme absorbed | 357 | 8375 | 84 |
| Activity in carrier | 236 | 3272 | 68 |
| Activity after GA fixation | 250 | 2413 | 75 |

For the continuous hydrolysis the following columns were prepared using the above-mentioned enzyme preparations:

1. A 100 ml column was filled with 19.9 g of dry enzyme/CMC carrier composition. Activities after fixing with glutaraldehyde were:

| | |
|---|---|
| β-xylosidase | 300 nkat/g |
| xylanase | 3180 nkat/g |
| esterase | 137 nkat/g |

2. A 100 ml column was filled with 26.3 g of dry enzyme/DUOLITE composition. Activities after fixing with glutaraldehyde were:

| | |
|---|---|
| β-xylosidase | 250 nkat/g |
| xylanase | 2413 nkat/g |
| esterase | 75 nkat/g |

3. A 50 ml column was filled with 12.5 g of dry enzyme/CMC carrier composition. No fixing was carried out. Activities were

| | |
|---|---|
| β-xylosidase | 346 nkat/g |
| xylanase | 2970 nkat/g |
| esterase | 126 nkat/g |

4. A 50 ml column was filled with 14.5 g of dry enzyme/DUOLITE composition. No fixing was carried out. Activities were:

| | |
|---|---|
| β-xylosidase | 236 nkat/g |
| xylanase | 3272 nkat/g |
| esterase | 68 nkat/g |

The substrate to be hydrolysed was a steam-exploded birch wood extract (steam-explosion conditions 210° C., 4 minutes) containing 11 g/l xylose and 23 g/l xylan oligomers. The total dry substance content of the solution was 70 g/l, and the pH was adjusted to 5. The filtrated solution was fed to the bottom of each column and its flow rate in the columns 1 to 4 was 14.4 ml/h, 15.0 ml/h, 6.9 ml/h and 6.8 ml/h, respectively. The temperature was 45° C. The xylose in the eluate was measured after 2, 4 and 7 days. The results are shown in the following TABLE 5.

TABLE 5

Xylose content in the eluate
(grams per liter of solution and % of dry substance)

| Time | CMC/GA | | DUOLcat/GA | | CMC | | DUOLcat | |
|---|---|---|---|---|---|---|---|---|
| days | g/l | % | g/l | % | g/l | % | g/l | % |
| 2 | 29.2 | 41.6 | 33.4 | 47.8 | 25.6 | 36.6 | 35.1 | 50.1 |
| 4 | 26.9 | 38.4 | 31.0 | 44.2 | 24.3 | 34.7 | 32.9 | 47.0 |
| 7 | 22.5 | 32.1 | 33.1 | 47.3 | 25.4 | 36.2 | 32.4 | 46.2 |

The results show that the column activities were not significantly impaired during the 7-day experiment. The fixation with glutaraldehyde had no effect on the column stability.

EXAMPLE 3

Immobilized enzymes were tested in the hydrolysis of a hemicellulose solution from steam-exploded birch-wood.

The immobilization was carried out as described in Example 1, except that the temperature was 22° C. No fixation with glutaraldehyde was carried out.

Carriers:
1. Cellulose-based CMC carrier; particle size 350–850 μm; ion-exchange capacity 0.15 mequiv/ml; density 0.25–0.38 g/ml.
2. DUOLITE C 464; pH 3.8; water content 57–62%; density 0.75 g/ml.

Enzyme solution:

| | |
|---|---|
| β-xylosidase | 5400 nkat/ml |
| esterase | 400 nkat/ml |
| xylanase | 99100 nkat/ml. |

Immobilization:

| | | |
|---|---|---|
| 1. | 50 ml | enzyme solution |
| | 25 ml | 0.05 M citrate buffer pH 5 |
| | 37.5 g | CMC carrier |
| 2. | 50 g | enzyme solution |
| | 25 ml | 0.05 M citrate buffer pH 5 |
| | 37.5 g | DUOLITE C 464 carrier |

For each experiment the column was filled with the immobilized enzymes and the birch wood hydrolysate was fed through the column. The concentration of the hydrolysate was 9.0% by weight and pH 5. The composition contained xylose 10 g/l and oligomers 32 g/l. The temperature was 45° C. The solution was fed slowly through the column so that the total hydrolysis time was 4 hours. The column experiment was continued 26 days in order to check possible in activation of the immobilized enzyme, and the xylose concentration in the solution was determined. The theoretical xylose yield is 55% on dry substance.

The results are shown in the following TABLE 6.

TABLE 6

Hydrolysis of xylan to xylose in a continuous
process utilizing immobilized enzymes

| Time days | CMC carrier % xylose of d. s. | DUOLITE carrier % xylose of d. s. |
|---|---|---|
| 1 | 56 | 53 |
| 4 | | 48 |
| 5 | 57 | |
| 9 | 49 | 42 |
| 14 | 42 | |
| 15 | | 40 |
| 20 | 40 | |
| 21 | 49 | 42 |
| 26 | 44 | |

The conversion rate is very high, close to the theoretical value (55% with free enzymes). No significant inactivation was observed during the experiment period.

The carriers can be regenerated by washing out the inactivated enzyme with alkaline solution, activating with acid, washing with water and feeding fresh enzyme into the column. The enzyme is immobilized on the carrier and the process can continue.

EXAMPLE 4

Hydrolysis with immobilized enzyme was carried out on two xylo-oligomer solutions: Solution 1 was obtained from a chromatographic separation of a birch wood hydrolysate, solution 2 was a steam-exploded birch wood extract which was subjected to pre-hydrolysis with free (not immobilized) enzymes. Before prehydrolysis the compositions of the solutions were as follows:

|                          | Solution 1 | Solution 2 |
|--------------------------|------------|------------|
| Dry subst., % by weight  | 7.0        | 12.5       |
| pH                       | 5.3        | 3.3        |
| Xylose, g/l              | 7.4        | 16         |
| Xylo-oligomers g/l       | 42         | 43         |
| Conductivity, mS/cm      | 2.75       | 8.0        |

Solution 2 was prehydrolysed with free (not immobilized) enzyme to reduce the size of the polymers. A similar enzyme solution as in the following immobilization was used; the prehydrolysis temperature was 40° C. and pH 5.0. 0.015 ml of enzyme solution was added per g substrate. After prehydrolysis the solution was filtrated. The obtained prehydrolysed solution 2 contained xylose 30 g/l.

The hemicellulase enzymes obtained by fermentation with Trichoderma were immobilized on a weak cation exchanger (DUOLITE C 464) by mixing for 4 hours in a pH-5 citrate buffer at room temperature ($\approx$20 to 24° C.). Enzyme activities were measured:

| xylanase     | 47000 nkat/g |
| esterase     | 174 nkat/g   |
| $\beta$-xylosidase | 1200 nkat/g  |

The $\beta$-xylosidase immobilization yield was 100%, the xylanase yield 76% and the esterase yield 70%.

The hydrolysis was carried out in a column as a continuous process under the following conditions:

| Column volume | 10 ml                     |
| Flow rate     | 1 column volume per hour  |
| Temperature   | 45° C.                    |

Results when the column had been in use 15 days:

|                              | Solution 1 | Solution 2 |
|------------------------------|------------|------------|
| Xylose, g/l                  |            |            |
| feed solution                | 7.4        | 30         |
| after hydrolysis             | 36         | 51         |
| Glucose, g/l                 | 2          | 3          |
| after hydrolysis             |            |            |
| Arabinose, g/l               | 3          | 4          |
| after hydrolysis             |            |            |
| Galactose, g/l               | 1          | 3          |
| after hydrolysis             |            |            |
| Oligomers, g/l               | 12         | 18         |
| after hydrolysis             |            |            |

There was no serious deterioration or exhaustion of the column during the 15-day experiment. In order to examine the regeneration the column was washed with sodium hydroxide, activated with acid, washed with water and loaded with fresh enzyme.

EXAMPLE 5

Duolite C 464 and CMC carriers were used in the regeneration experiments.

The carrier was washed in the column with 0.5 M sodium hydroxide (4 column volumes) at 50° C. The carrier was then restored with 0.5 M sulphuric acid, rinsed with water and buffered with citrate buffer to pH 5.

Fresh enzyme wad added to the column and immobilized (no fixing additives). 100 column volumes of steam-exploded birch wood extract was fed into the column. The cycle was repeated 6 times. The results are shown in the following TABLE 7.

TABLE 7

Repeated immobilization (regeneration of columns)

Enzyme activity, nkat/g carrier

|                | $\beta$-xylosidase | esterase | xylanase |
|----------------|--------------------|----------|----------|
| CMC carrier | | | |
| Experiment 1   |        |     |         |
| offered        | 1936   | 264 | 319200  |
| bound          | 1312   | 150 | 163300  |
| Experiment 2   |        |     |         |
| offered        | 2420   | 330 | 415800  |
| bound          | 1092   | 129 | 139300  |
| Experiment 3   |        |     |         |
| offered        | 1632   | 192 | 163800  |
| bound          | *      | 44  | *       |
| Experiment 4   |        |     |         |
| offered        | 2750   | 155 | 415800  |
| bound          | 1367   | *   | 193900  |
| Experiment 5   |        |     |         |
| offered        | 2750   | 275 | 300200  |
| bound          | 1014   | 98  | 21300   |
| DUOLITE C 464 carrier | | | |
| Experiment 1   |        |     |         |
| offered        | 962    | 133 | 319200  |
| bound          | 956    | 93  | 144500  |
| Experiment 2   |        |     |         |
| offered        | 1285   | 178 | 2151000 |
| bound          | 1278   | 169 | 205000  |
| Experiment 3   |        |     |         |
| offered        | 844    | 101 | 84700   |
| bound          | 791    | 57  | 15700   |
| Experiment 4   |        |     |         |
| offered        | 1426   | 80  | 215600  |
| bound          | 1282   | 47  | 179900  |
| Experiment 5   |        |     |         |
| offered        | 1419   | 142 | 155000  |
| bound          | 1375   | 92  | 134000  |
| Experiment 6   |        |     |         |
| offered        | 1165   | 142 | 186400  |
| bound          | *      | 51  | 38500   |

*not measured

It appears from the results that the binding of $\beta$-xylosidase to the DUOLITE carrier remained almost unchanged whereas the binding of the two other enzymes was slightly deteriorated. The regeneration of the CMC carrier was not quite as successful but the binding of all the enzymes deteriorated to some extent. The experiments showed that the immobilization could be repeated several times on the same carrier without significant reduction in the absorption capacity.

EXAMPLE 6

This experiment was carried out to study the binding of an individual hemicellulase enzyme, $\beta$-xylosidase on a weak cation exchange carrier and its ability to hydrolyse xylo-oligomers.

An enzyme solution produced by *Trichoderma longibrachiatum* and having the following activities:

| | |
|---|---|
| Xylanase | 200000 nkat/ml |
| Acetyl esterase | 1000 nkat /ml |
| β-xylosidase | 4200 nkat/ml | was separated into two fractions (A and B) by adding ammonium sulphate 20% on the weight of the solution, stirring lightly and allowing to stand at +4° C. for 24 hours. The fractions were separated by centrifugation for 5 minutes at 2000 rpm. The β-xylosidase was enriched in the solution fraction A with a yield of 54%, the obtained purity being 3.3-fold. The amounts of other xylanolytic enzymes in this fraction were very small (see TABLE 8). The β-xylosidase was further purified by ultrafiltration (UF) of the fraction A with an A Amicon ultra filter PM 10 having a separating range of MP 10,000, until the salt content of the solution was 4%. The removal of the salt involved a further increase in the degree of purity of the β-xylosidase (see TABLE 8).

TABLE 8

Fractionation of hemicellulase with ammonium sulphate

| | Specific activity nkat/mg protein | | | |
|---|---|---|---|---|
| | | Fractions | | Ultrafiltration |
| | Hemicellulase | A | B | fraction |
| Xylanase | 1430 | 130 | 1680 | 42 |
| β-xylosidase | 30 | 100 | 12 | 195 |
| Acetylesterase | 7.5 | 0.4 | 9 | 0.6 |

β-xylosidase was immobilized on DUOLITE C 464 using 60 ml of ultrafiltration fraction A (β-xylosidase 4600 nkat/ml) and 20 ml resin which were mixed for 1 hour at 25° C. and ph 3.7. After washing the resin contained bound β-xylosidase 11000 nkat/ml.

The β-xylosidase so immobilized was used in the hydrolysis of xylo-oligomers from a steam-exploded birch wood extract which was prehydrolysed enzymatically to cleave xylan and acetyl side chains. In the prehydrolysis the enzyme amounts per g dry substance were: xylanase 1280 nkat, β-xylosidase 25 nkat and acetyl esterase 7 nkat; the hydrolysis period was 24 hours, pH 5 and temperature 45° C. Composition of the extract used in the prehydrolysis was:

| | |
|---|---|
| Dry substance, % | 10 |
| pH | 4.3 |
| Conductivity, mS/cm | 7 |
| Carbohydrates | |
| xylose, % on weight of sol. | 1.3 |
| glucose, % on weight of sol. | 0.1 |
| oligosaccharides % on weight of sol. | 4.5 |

Prehydrolysed extract was fed through a carrier column containing immobilized β-xylosidase under the following conditions:

| | |
|---|---|
| Column volume | 10 ml |
| Flow rate | 2 column volumes/h |
| Temperature | 45° C. |
| pH | 4.3 |

Hydrolysis with immobilized enzyme was continued as a continuous process for 30 days, whereafter the solution was assayed for its xylose and oligosaccharide content. The results were as follows:

| | Concentration, g/100 g | |
|---|---|---|
| | xylose | oligosaccharides |
| Steam-exploded birch wood extract | | |
| - as such | 1.3 | 4.5 |
| - enzymatically prehydrolysed | 2.5 | 3.3 |
| - prehydrolysate hydrolysed further with immobilized β-xylosidase | 5.0 | 0.8 |

Reduction in the xylose yield during the observing period (30 days) was only 5% as compared with the initial values.

EXAMPLE 7

Immobilized hemicellulase was tested in the hydrolysis from xylo-oligomers contained in a beech prehydrolysate from a side product obtained from Celuloza Swiecie, Poland. The xylo-oligomers of the beech prehydrolysate were purified by chromatographic separation before hydrolysis with immobilized hemicellulase, and its composition was as follows:

| | | |
|---|---|---|
| Dry substance, % | | 7.3 |
| pH | | 5.4 |
| Color (Icumsa, pH 5) | | 184000 |
| Conductivity, mS/cm | | 4 |
| Carbohydrates | | |
| - xylose | 0.7%* | 9.5%** |
| - glucose | 0.5%* | 7.0%** |
| - oligosaccharides | 3.9%* | 53.5%** |

*on the weight of the solution
**on dry substance

The immobilization was carried out with the hemicellulase preparation mentioned in Example 6. In the immobilization, hemicellulase was used 0.5 ml/g DUOLITE C 464 carrier, and the binding was effected by stirring for 4 hours at 25° C. at pH 4.5. Amounts bound to the DUOLITE C 464 were

| | |
|---|---|
| Xylanase | 78960 nkat/g resin on native weight |
| β-xylosidase | 2050 nkat/g resin on native weight |
| Acetyl esterase | 250 nkat/g resin on native weight |

The beech prehydrolysate was hydrolysed in a continuously operating column under the following conditions:

| | |
|---|---|
| Column volume | 10 ml |
| Flow rate | 2 column volumes/h |
| pH | 5.5 |
| Temperature | 40° C. |

The following xylose yields were obtained during the running of the column:

| Running time, days | Xylose, w - % on solution | Xylose, w - % on d. s. |
|---|---|---|
| 1 | 2.9 | 40.1 |
| 3 | 3.0 | 41.0 |
| 6 | 2.65 | 36.3 |

-continued

| Running time, days | Xylose, w-% on solution | Xylose, w-% on d. s. |
|---|---|---|
| 7 | 2.65 | 36.3 |
| 14 | 2.65 | 36.3 |
| 18 | 2.65 | 36.3 |

We claim:

1. A process for the production of xylose by the hydrolysis of a hemicellulose substrate containing xylo-oligomers with an immobilized enzyme having hemicellulolytic activity comprising the steps of:
   a) adjusting the pH of an aqueous solution containing hemicellulose oligosaccharide to a value within a range of about 3.5 to 5.0;
   b) contacting the solution with an immobilized enzyme composition having hemicellulolytic activity and containing an effective amount of β-xylosidase to produce xylose, wherein said enzyme composition is produced by a microorganism of the genus Trichoderma and wherein said enzyme composition is immobilized on a regenerable weak cation exchange carrier without the addition of fixing additives; and
   c) recovering xylose from the solution.

2. The process according to claim 1, wherein said immobilized enzyme is an enzyme obtained from a microorganism of the species *Trichoderma longibrachiatum* or *Trichoderma reesei*.

3. The process according to claim 1 or 2, wherein said weak cation exchange carrier is an agglomerated carboxymethyl cellulose strengthened with polystyrene.

4. The process according to claim 3, wherein the hemicellulose substrate containing xylo-oligomers comprises liquor obtained during or after a cellulose cooking process.

5. The process according to claim 3, wherein the hemi cellulose substrate containing xylo-oligomers is a water extract of xylan-containing steam-exploded plant material or of enzymatically prehydrolyzed xylan-containing steam-exploded plant material.

6. The process according to claim 1 or 2, wherein said weak cation exchange carrier is DUOLITE C 464.

7. The process according to claim 6, wherein the hemicellulose substrate containing xylo-oligomers comprises liquor obtained during or after a cellulose cooking process.

8. The process according to claim 6, wherein the hemicellulose substrate containing xylo-oligomers is a water extract of xylan-containing steam-exploded plant material or of enzymatically prehydrolyzed xylan-containing steam-exploded plant material.

9. The process according to claim 1, wherein the hemicellulose substrate containing xylo-oligomers comprises liquor obtained during or after a cellulose cooking process.

10. The process according to claim 1, wherein the hemicellulose substrate containing xylo-oligomers is a water extract of xylan-containing steam-exploded plant material or of enzymatically prehydrolyzed xylan-containing steam-exploded plant material.

11. The process according to claim 1, wherein the aqueous solution containing hemicellulose oligosaccharide has a conductivity between 2 and about 8 mS/cm.

12. The process according to claim 2, wherein the hemicellulose substrate containing xylo-oligomers comprises liquor obtained during or after a cellulose cooking process.

13. The process according to claim 2, wherein the hemicellulose substrate containing xylo-oligomers is a water extract of xylan-containing steam-exploded plant material or of enzymatically prehydrolyzed xylan-containing steam-exploded plant material.

* * * * *

UNITED STATES PATENT AND TRADEMARK OFFICE
CERTIFICATE OF CORRECTION

PATENT NO. : 5,932,452
DATED : August 3, 1999
INVENTOR(S) : Annikka Mustranta, et. al.

It is certified that error appears in the above-identified patent and that said Letters Patent is hereby corrected as shown below:

In the title page, in [22] PCT filed:

Change "Sep. 21, 1990" to - - Sep. 3, 1990 - -.

Column 3, line 33, change "is" to - - its - -.

Column 5, line 11, change "suphate" to - - sulphate - -.

Column 8, line 52, change "absorbed" to - - adsorbed - -.

Column 10, line 31, change "in activation" to - - inactivation - -.

Column 11, line 65, change "wad" to - - was - -.

Column 12, line 34, change "2151000" to - - 215100 - -.

Signed and Sealed this

First Day of May, 2001

Attest:

NICHOLAS P. GODICI

Attesting Officer

Acting Director of the United States Patent and Trademark Office